United States Patent
Walcott et al.

(10) Patent No.: US 11,481,069 B2
(45) Date of Patent: Oct. 25, 2022

(54) PHYSICAL CURSOR CONTROL IN MICROFLUIDIC DISPLAY DEVICES

(71) Applicant: INTERNATIONAL BUSINESS MACHINES CORPORATION, Armonk, NY (US)

(72) Inventors: Aisha Walcott, Nairobi (KE); Sarbajit K. Rakshit, Kolkata (IN); Catherine H. Crawford, Bedford, NH (US); John A. Gunnels, Somers, NY (US)

(73) Assignee: International Business Machines Corporation, Armonk, NY (US)

( * ) Notice: Subject to any disclaimer, the term of this patent is extended or adjusted under 35 U.S.C. 154(b) by 177 days.

(21) Appl. No.: 17/021,191

(22) Filed: Sep. 15, 2020

(65) Prior Publication Data
US 2022/0083195 A1 Mar. 17, 2022

(51) Int. Cl.
| | |
|---|---|
| *G06F 3/041* | (2006.01) |
| *A61F 4/00* | (2006.01) |
| *G16H 50/20* | (2018.01) |
| *G06N 3/04* | (2006.01) |
| *G16H 50/30* | (2018.01) |

(52) U.S. Cl.
CPC ............ *G06F 3/04186* (2019.05); *A61F 4/00* (2013.01); *G06F 3/041* (2013.01); *G06N 3/0445* (2013.01); *G16H 50/20* (2018.01); *G16H 50/30* (2018.01)

(58) Field of Classification Search
CPC ........ G06F 3/04186; G06F 3/041; A61F 4/00; G06N 3/0445; G16H 50/20; G16H 50/30
See application file for complete search history.

(56) References Cited

U.S. PATENT DOCUMENTS

| | | | | |
|---|---|---|---|---|
| 8,203,537 | B2* | 6/2012 | Tanabe | G06F 3/04886 345/173 |
| 8,619,035 | B2* | 12/2013 | Ciesla | G06F 3/016 340/407.2 |
| 9,836,126 | B2 | 12/2017 | Ekambaram | |
| 9,921,651 | B2 | 3/2018 | Rakshit | |
| 10,096,264 | B2 | 10/2018 | Robinson | |
| 10,437,359 | B1* | 10/2019 | Wang | G06F 3/016 |

(Continued)

FOREIGN PATENT DOCUMENTS

| | | |
|---|---|---|
| CN | 103513908 A | 1/2014 |
| CN | 104657077 A | 5/2015 |

OTHER PUBLICATIONS

Goril, "iOS 13 Changes the Way You Navigate & Edit Text—Here's How to Place the Cursor, Make Selections, Perform Edits & More," GADGETHACKS, Aug. 27, 2019, pp. 1-13.

(Continued)

*Primary Examiner* — David D Davis
(74) *Attorney, Agent, or Firm* — David Spalding

(57) ABSTRACT

Physical assistance for identification of an input location on a touchscreen may include detecting that a user has contacted a touchscreen at an initial touch point with a pointing device, predicting an input location from one or more input locations for receiving input on the touchscreen, determining a path from the initial touch point to the predicted input location, and generating a physical cursor on the touchscreen at a location proximate to the pointing device, wherein the physical cursor is a raised portion of the touchscreen.

20 Claims, 8 Drawing Sheets

(56) References Cited

U.S. PATENT DOCUMENTS

| | | | |
|---|---|---|---|
| 2011/0157080 A1* | 6/2011 | Ciesla | G06F 3/0202 345/173 |
| 2011/0304550 A1* | 12/2011 | Romera Jolliff | G06F 3/016 715/810 |
| 2013/0021303 A1* | 1/2013 | Martin | G06F 1/3262 345/178 |
| 2013/0044100 A1 | 2/2013 | King | |
| 2013/0155020 A1* | 6/2013 | Heubel | G06F 3/04886 345/174 |
| 2013/0249832 A1* | 9/2013 | Nakamura | G06F 3/041 345/173 |
| 2014/0002393 A1 | 1/2014 | Bao | |
| 2014/0160064 A1* | 6/2014 | Yairi | G06F 3/04166 345/174 |
| 2015/0185988 A1 | 7/2015 | Yim | |
| 2016/0132139 A1 | 5/2016 | Du | |
| 2016/0202761 A1* | 7/2016 | Bostick | G09B 21/004 345/173 |
| 2017/0025097 A1* | 1/2017 | Kuribayashi | G06F 3/0444 |
| 2017/0168575 A1* | 6/2017 | Kasahara | G06F 3/0446 |
| 2017/0263146 A1* | 9/2017 | Aggarwal | G09B 19/003 |

OTHER PUBLICATIONS

Johnston, "Microfluids Panel Could Add Physical Buttons to a Touch Screen," ARSTECHNICA, https://arstechnica.com/gadgets/2014/01/new-microfluidics-panel-could-add-physical-buttons-to-a-touch-screen/, Jan. 23, 2014, pp. 1-4.

Orf, "Tactile Keyboards That Rise Out of Touchscreens Are Finally Here," GIZMODO, Tactus Technology, https://arstechnica.com/gadgets/2014/01/new-microfluidics-panel-could-add-physical-buttons-to-a-touch-screen/, Feb. 12, 2015, pp. 1-5.

International Search Report and Written Opinion of International Application No. PCT/CN2021/115521, dated Nov. 26, 2021, 9 pages.

Walcott et al., "Physical Cursor Control in Microfluidic Display Devices," International Application No. PCT/CN2021/115521, filed Aug. 31, 2021, 28 pages.

* cited by examiner

PHYSICAL CURSOR CONTROL IN MICROFLUIDIC DISPLAY DEVICES

BACKGROUND

The present invention relates to providing physical assistance to user input, and more specifically to providing a physical cursor through microfluidics on a touchscreen to assist in providing manual input for controlling a cursor.

SUMMARY

An embodiment is directed to method for physically assisting in the identification of an input location on a touchscreen. The method may include detecting that a user has contacted a touchscreen at an initial touch point with a pointing device, predicting an input location from one or more input locations for receiving input on the touchscreen, determining a path from the initial touch point to the predicted input location, and generating a physical cursor on the touchscreen at a location proximate to the pointing device, wherein the physical cursor is a raised portion of the touchscreen.

Additional embodiments are directed to a system and computer program product for physically assisting in the identification of an input location on a touchscreen.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DETAILED DESCRIPTION

For some individuals with limited motor movement in their hands and/or visual impairment, it can be difficult to control the position of a conventional cursor on a touchscreen device. Other users may want to provide input to a touchscreen device at a time when the user is not looking at a display. Some examples are when the cursor is between text fields or if a user wishes to directly move a progress bar for video content, or if a user simply wants to guide the cursor to a specific location. In the case of these users, precisely moving the cursor is problematic, especially for those visually impaired users or those with disorders affecting the central nervous system such as multiple sclerosis (MS), Parkinson's disease, tardive dyskinesia (TD), or the elderly.

Figure 1A:
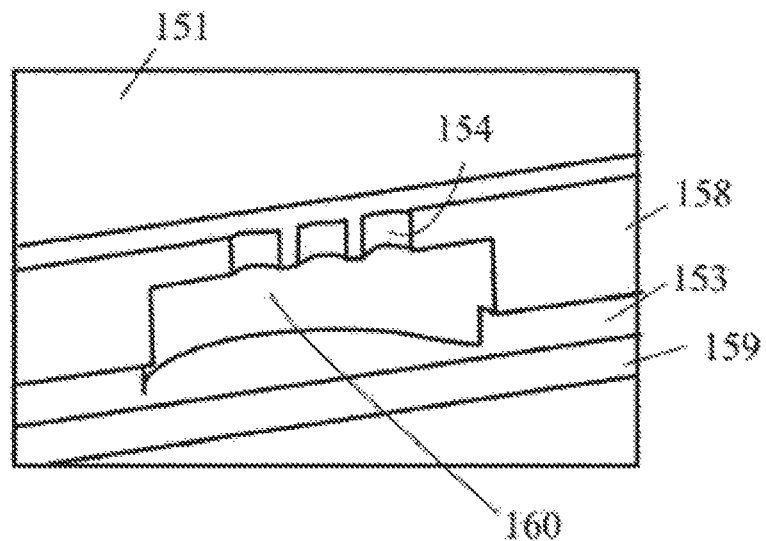
FIG. 1A shows a cut-away cross-sectional view of a touchscreen.

FIG. 1A shows a touchscreen of a computer system ("system"). At least a portion of the touchscreen has multiple layers. A first layer 151 is the touch interface which the user directly interacts with. A second layer 158 is present between the first layer 151 and a third layer 159. The second layer 158 has a plurality of holes 154. The plurality of holes 154 may be placed throughout the screen. A reservoir 160 is formed between the second layer 158 and the third layer 159 and is in fluid communication with the plurality of holes 154 and one or more passages 153 formed between the second layer 158 and the third layer 159 in connection to a microfluidics supply (not shown). The plurality of holes may be distributed in various patterns, e.g., in a matrix pattern.

In one embodiment, one or more physical cursors or other objects for use with a particular web page or screen of an application may be rendered on the touch screen such that the physical cursor or other objects are overlaid on the touch screen where the fluid 156 can form ridges, buttons or any other desired shape. A processor or computer of the system preferably renders the physical cursor or other objects with at least one or more intersection points with microfluidic passages 153 and corresponding holes 154 and therefore a raised portion corresponding with a cursor or other object can be created on the touchscreen of the device.

FIG. 1A shows a cross-sectional view of a portion of a touchscreen in a position in which fluid 156 is not provided to the reservoir 160. When no fluid 156 is supplied to the reservoir 160, the entire first layer 151 of the touch screen 150 remains in contact with the second layer 158.

Figure 1B:
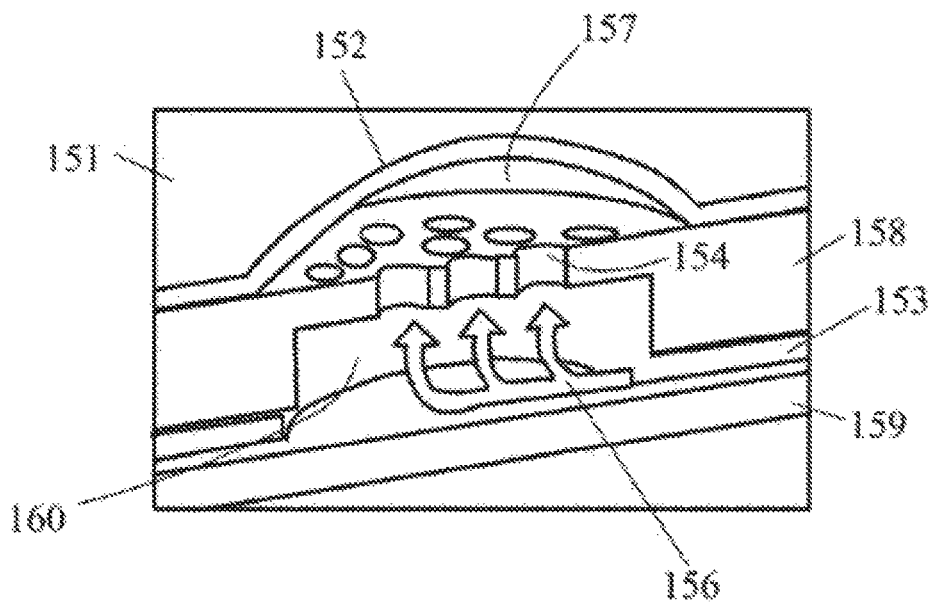
FIG. 1B shows a cut-away cross-sectional view of the touchscreen of FIG. 1A in which a portion of the screen is raised through microfluidics.

Referring now to FIG. 1B, the touchscreen is shown in a position in which fluid 156 is supplied from a supply (not shown) to the reservoir 160 through a passage 153. The fluid flows from the passage 153 and reservoir 160, through the holes 154 of the second layer 158 to form a pocket 157 of fluid between the first layer 151 and the second layer 158. The pressure of the fluid 156 causes the first layer 151 to separate from the second layer 158 and fill the pocket 157. The pocket 157 forms a bubble 152 or raised portion relative to the rest of the first layer 151. The raised bubble 152 will not generally be raised to a uniform height above the layer 151. In various embodiments, the raised bubble 152 may have a maximum height in a range of 0.25-5 mm. In one example, the raised portion 152 may have a maximum height of 1 mm. It should be noted that fluid may be supplied selectively to different portions of the touch screen 150. In addition, the bubble 152 or raised portion may be made to move to a series of locations on the touch screen by, for example, supplying fluid to a plurality of first locations adjacent to a first side of the bubble in succession while simultaneously removing the supply of fluid to a plurality of second locations adjacent to an opposite side of the bubble, as may be seen in FIGS. 2 and 3.

The cursors or other objects that are created by microfluidics as described above may be referred to herein as a "raised bubble" or "raised portion." The cursors or other objects that are created by microfluidics may also be referred to herein as a "physical cursor." It should be understood that these alternative terms have the same meaning and may be considered synonyms.

Figure 2:
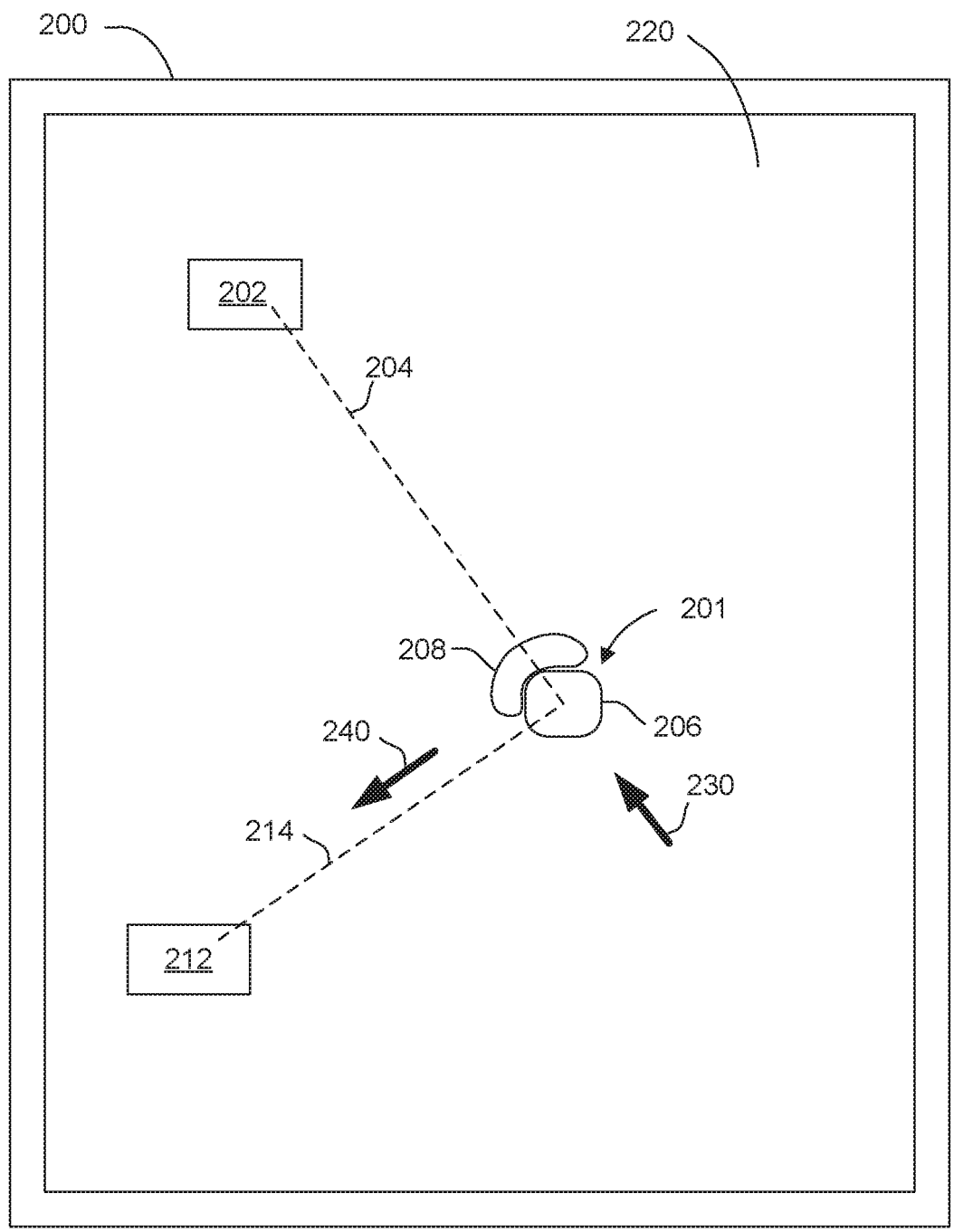
FIG. 2 is a diagram of a touchscreen display showing example input locations and a physical cursor according to an embodiment.
Figure 5A:
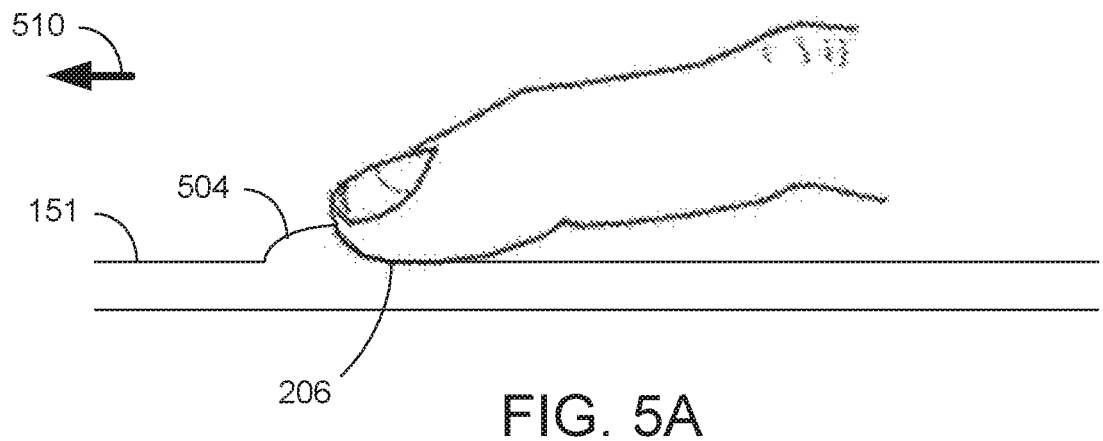
FIGS. 5A and 5B show side views of the physical cursors shown in FIGS. 2-4 according to various embodiments.

Referring now to FIG. 2, there is shown a plan view looking down on the touchscreen 220 where a device 200 may display a web page or screen of an application, according to an embodiment. The system may determine an input location 202 or 212 where an input may be required from a user. Multiple input locations 202 or 212 are shown to illustrate that the system may determine the input location 202 or 212 to be anywhere on the touchscreen 220 but only one input location is generally selected at a time. In an embodiment, this input location 202 or 212 may be a form field that requires data from the user. In other embodiments, this input location 202 or 212 may be a control related to an audio or video clip (such as volume or video progress) or may be a scroll bar for a software window. Once the user touches the screen 220, the system may detect an initial touchpoint 201 of the user's finger 206 on the touchscreen 220. It is not essential that the user interact with the touchscreen 220 using a finger; any pointing device suitable for use with a touchscreen, including a stylus, may be used in place of the user's finger. Paths 204 and 214 may be calculated between the touchpoint 206 and the respective input locations 202 or 212. Assume input location 202 is determined to be the input location where input is required from the user and the path 204 is calculated. Using the microfluidics technology of the device 200, the system may create a physical cursor 208 on the touchscreen by raising the display material into a small bubble just in front of the touchpoint 206 on the calculated path 204. The physical cursor 208 may be any suitable shape and, preferably, may conform to a front side of a finger or other pointing device. The physical cursor 208 may extend along one or two side portions of the finger or other pointing device. The physical cursor 208 may extend along a side portion of the finger or other pointing device partially (as shown in the figures) or completely (not shown in FIG. 2). It is not essential that the physical cursor 208 extend along a side portion of a finger or other pointing device; the physical cursor 208 may only be disposed between a "front" side of the finger, i.e., on a side of the finger on the path 204 between the input location 202 and the touchpoint 206. An example of a physical cursor 504 disposed on a "front" side of the finger is shown in a side view in FIG. 5A, where the physical cursor 504 moves in the direction of the arrow 510. As the system detects movement of the finger 206, the system may track this movement and continuously move the physical cursor 208 to match the movements of the user with their finger or other pointing device. The physical cursor 208 moves generally along path 204 to input location 202 as shown by arrow 230. If input location 212 was selected, physical cursor 208 would move generally along path 214 to input location 212 as shown by arrow 240. The system may also determine whether this movement is along the calculated path 204 and if the physical cursor 208 stays on the path 204, then the system would take no action other than advancing along the path 204. However, if the system determines that the user's finger 206 or other pointing device is off the path 204 or the cursor movement is stopped or moved in an unpredictable direction, the system may change the direction or position of the physical cursor movement such that the physical cursor 208 guides or leads the user's finger or other pointing device 206 in the direction of the input location 202.

Figure 3:
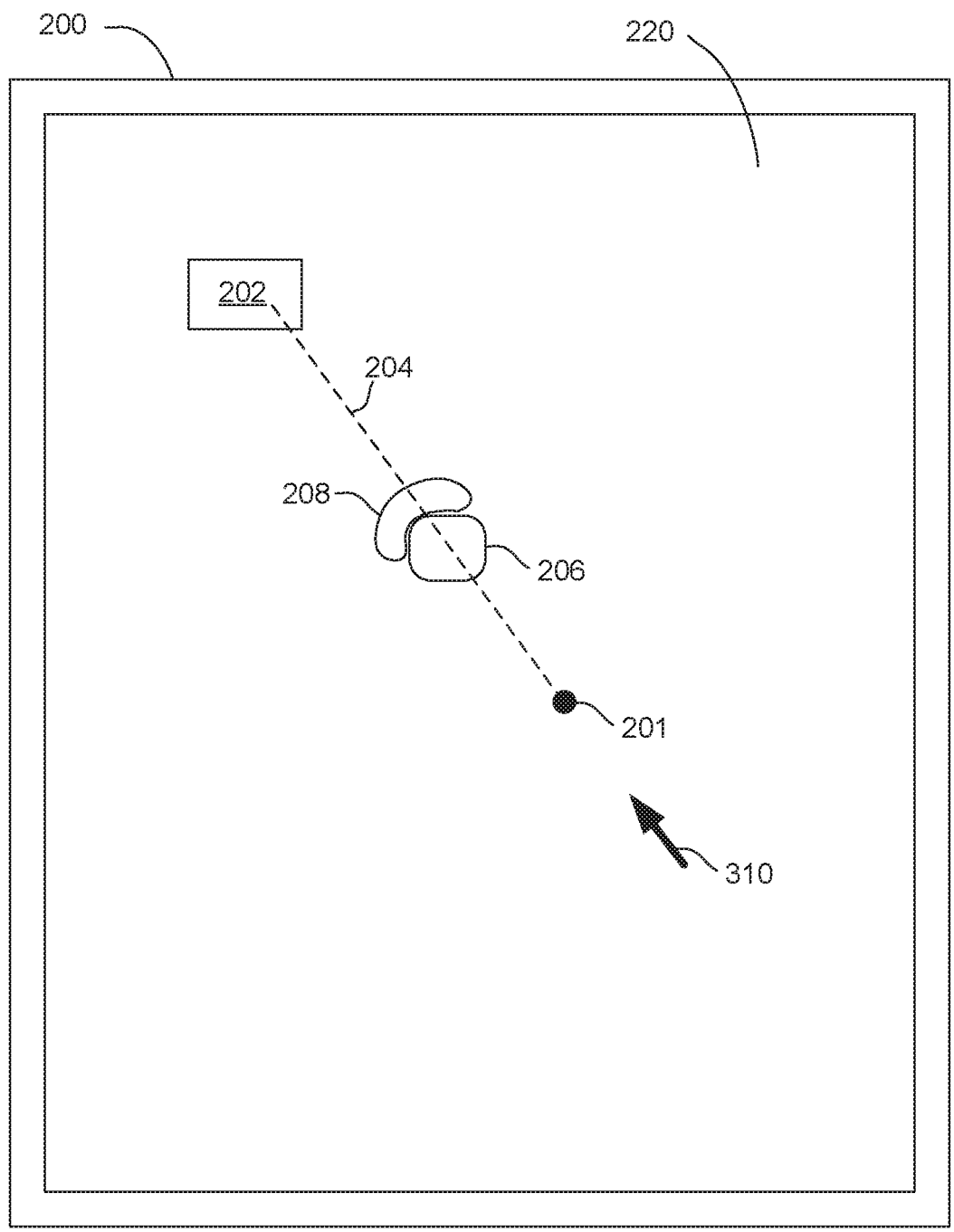
FIG. 3 is a diagram showing the touchscreen display and physical cursor of FIG. 2 illustrating movement of the physical cursor along a path between an initial touchpoint and an input location according to an embodiment.

FIG. 3 is a block diagram of the system with the physical cursor 208 in a new location to illustrate its potential movement along path 204. The system monitors the movement of the physical cursor 208 and finger or other pointing device 206 from the initial touchpoint 201 until the input location 202 is reached. In the example of FIGS. 2 and 3, FIG. 2 illustrates a position of the physical cursor 208 at a first time and FIG. 3 illustrates a position of the physical cursor 208 at a second time, which is subsequent to the first time. In this example, the physical cursor 208 may have been advanced along the path without deviation. Alternatively, the physical cursor 208 may have guided or nudged the user's finger or other pointing device 206 back to the path in response to movements to the right or left of the path. This guidance may occur at a time between the first and second times. It is to be understood in FIG. 3 that the physical cursor 208 moves generally along path 204 to input location 202 as shown by arrow 310.

Figure 4:
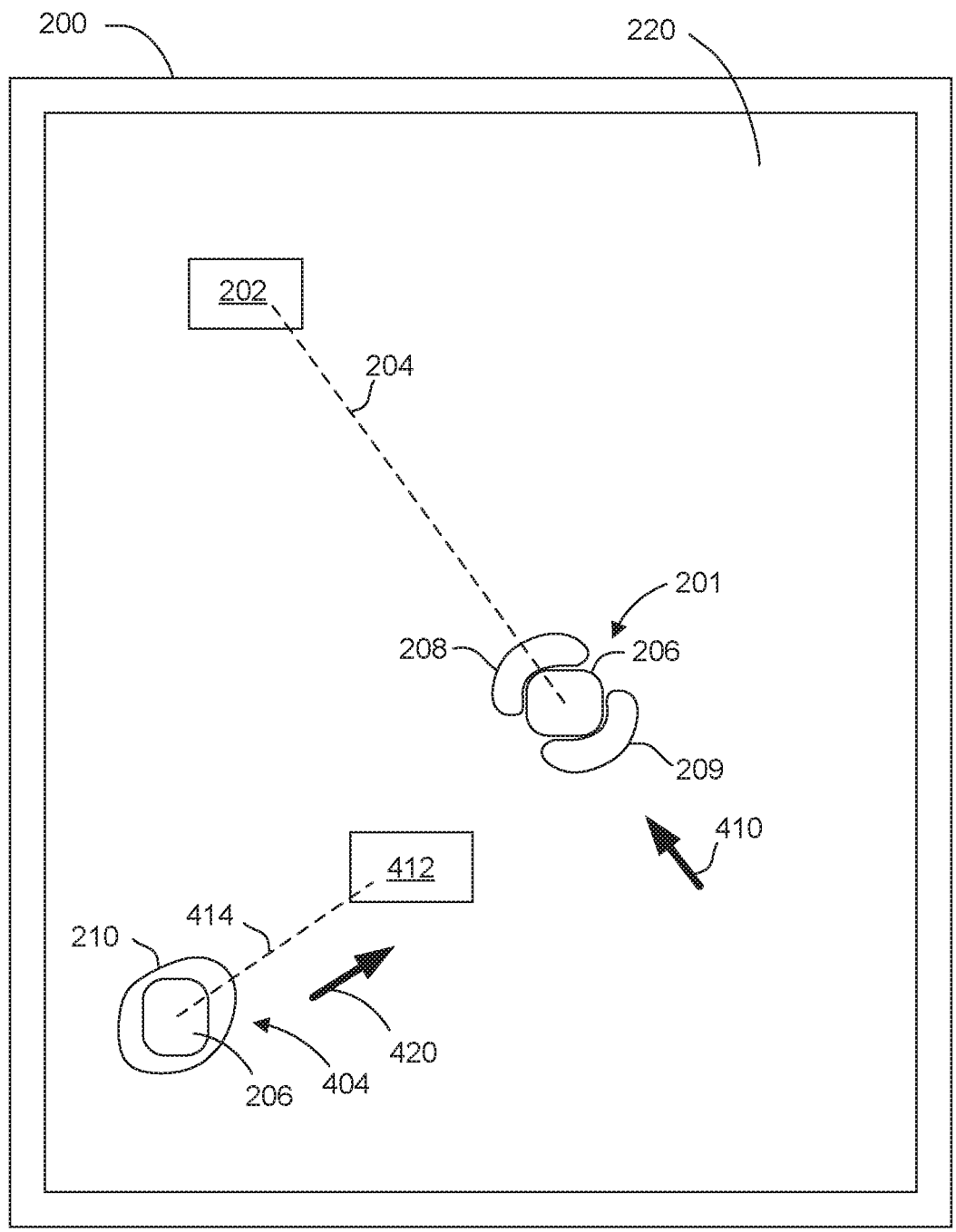
FIG. 4 is a diagram of the touchscreen display of FIG. 2 showing alternative embodiments of a physical cursor.

FIG. 4 is a plan view looking down on the touchscreen 220. In FIG. 4, a first example shows the input location 202, the user's finger or other suitable pointing device 206 at an initial touchpoint 201, the path 204 between the touchpoint 201 and the input location 202, and the physical cursor 208 that were presented in FIG. 2. In addition to the physical cursor 208, this first example shows an additional raised portion 209. Accordingly, in an embodiment, a finger or other pointing device may be simultaneously guided by the physical cursor 208 and guided or nudged by the additional raised portion 209 along the path 204. It is not essential that the "trailing" additional raised portion 209 be used with the "leading" physical cursor 208. In some embodiments, the "trailing" additional raised portion 209 alone may be used to guide or nudge a finger or other pointing device to an input location. In this first example, it is to be understood that the physical cursor 208 moves generally along path 204 to input location 202 as shown by arrow 410.

Figure 5B:
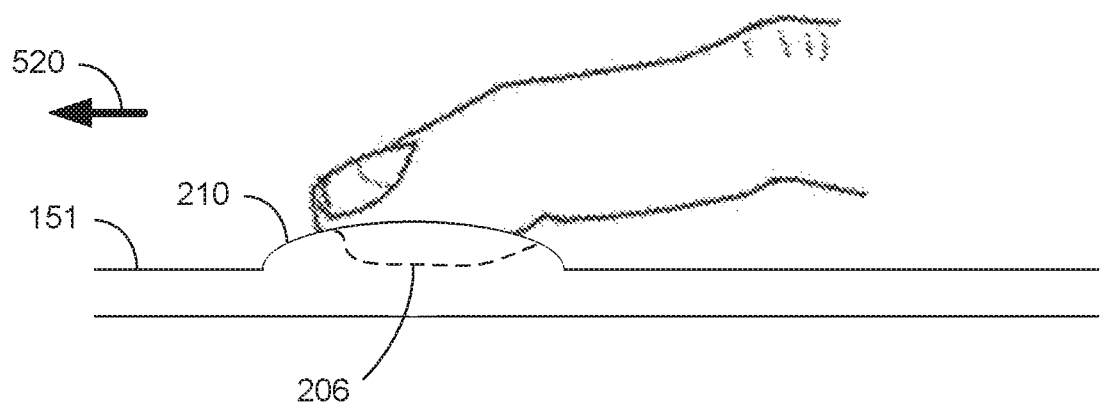

In FIG. 4, a second example shows an input location 412, the user's finger or other pointing device 206 at an initial touchpoint 404, a path 414 between the initial touchpoint 404 and the input location 412, and an alternative physical cursor 210 according to various embodiments. The alternative physical cursor 210 may be an oval or generally circular shape that surrounds and conforms to a finger or other pointing device. In this second example, it is to be understood that the alternative physical cursor 210 moves generally along path 414 to input location 412 as shown by arrow 420. FIG. 5B shows a side view of the alternative physical cursor 210 according to an embodiment where the alternative physical cursor 210 moves in the direction of the arrow 520.

Figure 6:
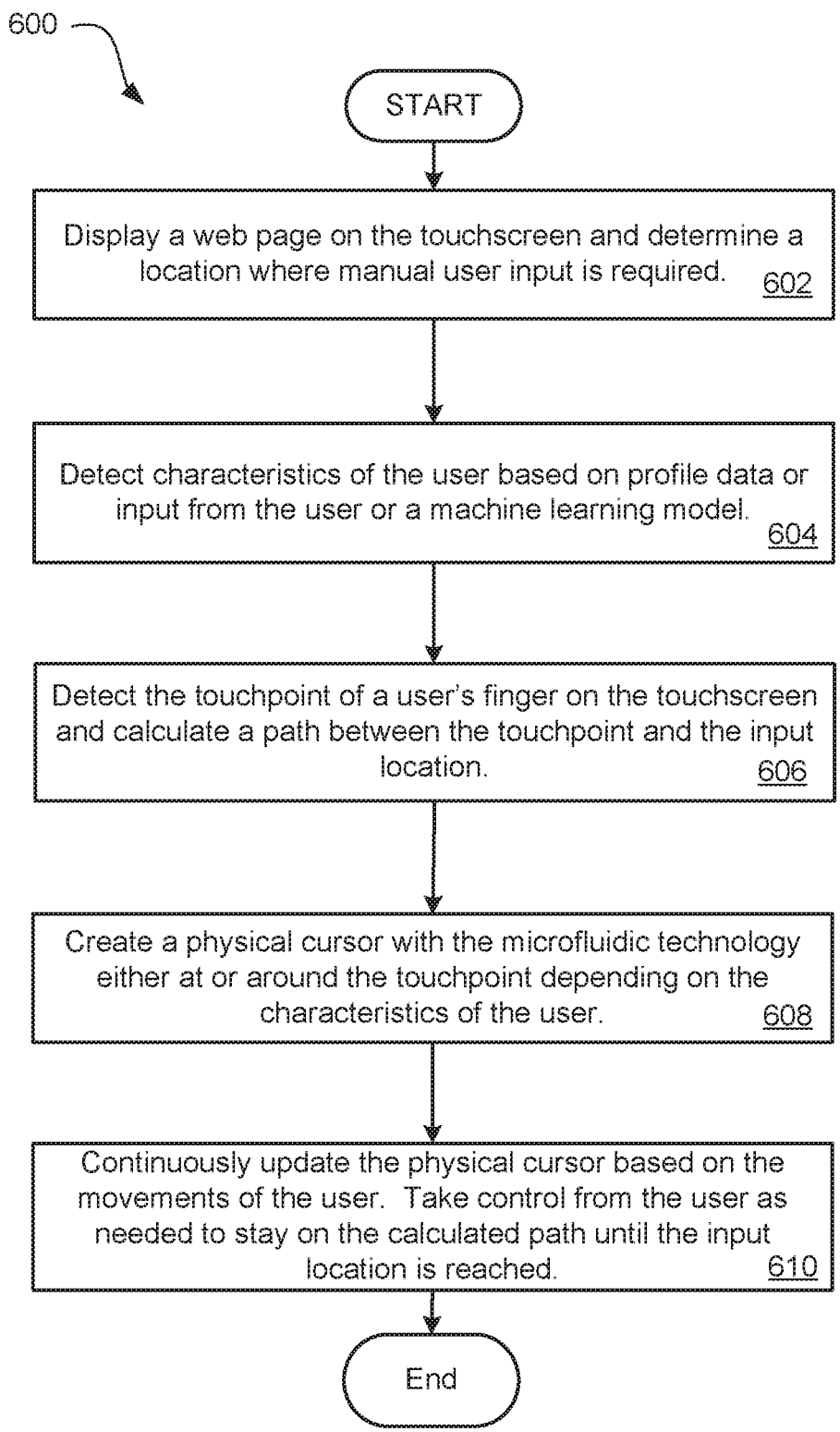
FIG. 6 is a flow chart of a physical cursor control process for a microfluidic display device in accordance with one or more embodiments.

Referring now to FIG. 6, a flow chart of a process 600 for creating and controlling a physical cursor on a microfluidic display device is shown. The process 600 may be performed by any computer system equipped with a touchscreen display. While the process 600 is described with reference to a computer system equipped with a touchscreen display, it should be understood that one or more steps or operations may be performed by a server or second computer remote from and in communication with the computer system equipped with a touchscreen display. At 602, a user interface screen, e.g., a web page or media player, is displayed on the touchscreen 220 and the displayed screen is analyzed to determine or predict an input location where manual user input may be required. In an embodiment, the touchscreen 220 may display a form that requires textual information to be entered into fields, i.e., input locations, and the system may determine that there are fields with data already entered and others that are empty and select the first one of the empty fields to the exclusion of those with data already entered. In another embodiment, the system may determine that all the data fields are filled in and select a submit button on the screen as the input location. In other embodiments, the input location may be an audio control or video progress control for a multimedia clip that is displayed in a media player on the touchscreen or a scroll bar on an active window that requires the user to drag the bar vertically to scroll the window. In yet another embodiment, e.g., when there are two or more input locations, the system may select the input location closest on the screen to the finger touchpoint as the input location.

At 604, the system may use a machine learning model such as a recurrent neural network to learn characteristic behavior of a user and to predict a sequence of locations for placing a physical cursor for the particular user on the touchscreen 220. In an embodiment, a sequential, recurrent neural network model may learn how the user historically interacts with the cursor and track the user's patterns, including mistakes and tremors, while controlling the movement of the cursor. Based on training data that includes user interaction patterns with the physical cursor or a conventional cursor, the model may be configured to determine the user's level of attention while moving a cursor or identify if the user requires special assistance in moving their hand or the physical cursor. The model may also determine the user's level of dexterity in deciding the level of assistance needed. In another embodiment, the system may use conventional camera images or ultrasound or infrared images to detect if the user is looking at the display while trying to move the physical cursor, and this information may be combined with the model's prediction of whether assistance is required due to lack of user focus on the display. In yet another embodiment, the model may account for the particular user's medical profile and may identify that the user is visually impaired or has difficulty controlling the movement of the cursor for a medical reason.

The model may also use the medical profile to obtain the user's medications and include medication data as a factor in predicting whether assistance is required and, if required, in determining adjustments in positioning of the physical cursor accordingly. The model may receive as input: time of day, usual or actual times of taking medication, and patterns, based on historical data, of hand tremor or shakiness of physical cursor movement throughout the day. In an embodiment, the model may predict that assistance is needed based on time of day, time of taking medication, and a historical hand tremor pattern. Consider, for example, a user who takes medication in the morning and experiences little or no tremor in the morning, but experiences increasing tremor as time elapses. The model may predict that cursor control assistance may be beneficial for this user in the afternoon or evening. In another embodiment, the model may predict that a user has missed taking medication at the prescribed time based on time of day, the prescribed time of taking medication, and a historical hand tremor pattern. For example, consider the same user who takes medication in the morning and has a pattern of no tremors in the morning, but a pattern of tremors later in the day. If the system detects trembling or shaky finger movement generally along a path from a touchpoint to an input location for this user in the morning, the system may determine that the user has not taken his or her medication at the required time and issue an alert to the user or a health care provider. In another embodiment, the model may predict that a medication causes a tremor. For example, consider a particular user that does not have a historical hand tremor pattern. If the system detects trembling or shaky finger movement generally along a path from a touch point to an input location for this user, the system may determine that a medication recently prescribed for this user is causing a tremor (as an undesired side effect) and may issue an alert to the user or a health care provider. The machine learning model and its inputs are further detailed in FIG. 7 below.

At 606, the system may detect the touchpoint of a user's finger or other pointing device on the touchscreen and calculate a path between the touchpoint and the input location using known methods.

At 608, the system may create a physical cursor on the touchscreen at or around the touchpoint with the microfluidic technology that is described in FIGS. 1A and 1B. An array of microfluidics ports may be spread across the entire display surface so that the cursor can be created at any position on the touchscreen display. The physical cursor may take any of a variety of different shapes at different locations relative to a finger or other pointing device. In an embodiment, the system may create a bubble that is just ahead of the user's finger to allow the user to push the physical cursor to the input location. In another embodiment, the system may create a physical cursor around or directly under the user's finger or other pointing device such that the finger or other pointing device will be carried to the input location. The type and size of physical cursor that is created may depend on the characteristics of the user detected at 604 and the level of assistance that the system determines is needed. For example, the size of a physical cursor may be adjusted to conform to a size or shape of a particular finger or other pointing device. As another example, a user experiencing a significant degree of difficulty navigating from an initial touchpoint to an input location, may be provided with a physical cursor that contacts or is placed proximate to the finger on two, three, or four sides, instead of one side. As yet another example, the system may determine that a user stays on the path better with a physical cursor in front of, behind or surrounding the finger or other pointing device, and selects the position and shape that provides closer or better adherence to the path. The system may make this determination based on historical date using physical cursors of different shapes. In another embodiment, based on the zoom level selection of the displayed text, the physical cursor size may be increased such that the dimension of the physical cursor may be aligned with text or other features displayed on the touchscreen.

In an embodiment, the system may also produce a haptic effect such as a vibration or other adjustment of the physical cursor in response to the user's movement in the event that the user is not attentive or is visually impaired and needs assistance in finding the position of the physical cursor relative to the underlying page displayed on the touch screen. The type of haptic effect and where it is used may be configured or selected by the user. In another example, if the cursor is moving vertically, it may move across the lines of text and the user could also understand the position of the physical cursor. In another example, if the physical cursor is being used with a progress bar or scroll bar for media or a program window is displayed, then the haptic effect could be enabled and allow a visually impaired user or one that is not looking at the display to find the position of the physical cursor in the progress bar on the scroll bar. After the physical cursor is found, the user can move the finger or other pointing device to change the position of the physical cursor.

At 610, the system may continuously update the location of the physical cursor based on the movements of the user. The system may take control from the user as needed to stay on the calculated path until the input location is reached. Once the physical cursor is created on the touchscreen, a stray or incorrect touch off the calculated path on the touchscreen should not affect the position of the physical cursor because the system may restrict any movement of the physical cursor that deviates from the path.

In an embodiment, once the input location is reached, the system may be configured to recognize that the user wants to select certain content within the input location area by applying pressure equal to or greater than a threshold level of pressure while touching the physical cursor at the same time. For example, an input area may include a check box or boxes for "yes" and "no". The user could also move their finger or other pointing device over words of text while applying pressure and accordingly, a desired textual area could be selected. The system may allow the user to feel the selected area physically and also raise the surface of the selected text. In another embodiment, the system may use the haptic effect described above, e.g., a vibration or other adjustment of the physical cursor, to alert the user that the input location has been reached. In some embodiments, the system may gradually remove the physical cursor from the screen as it nears the input location, such that it is gone once the user is at the input location.

Figure 7:
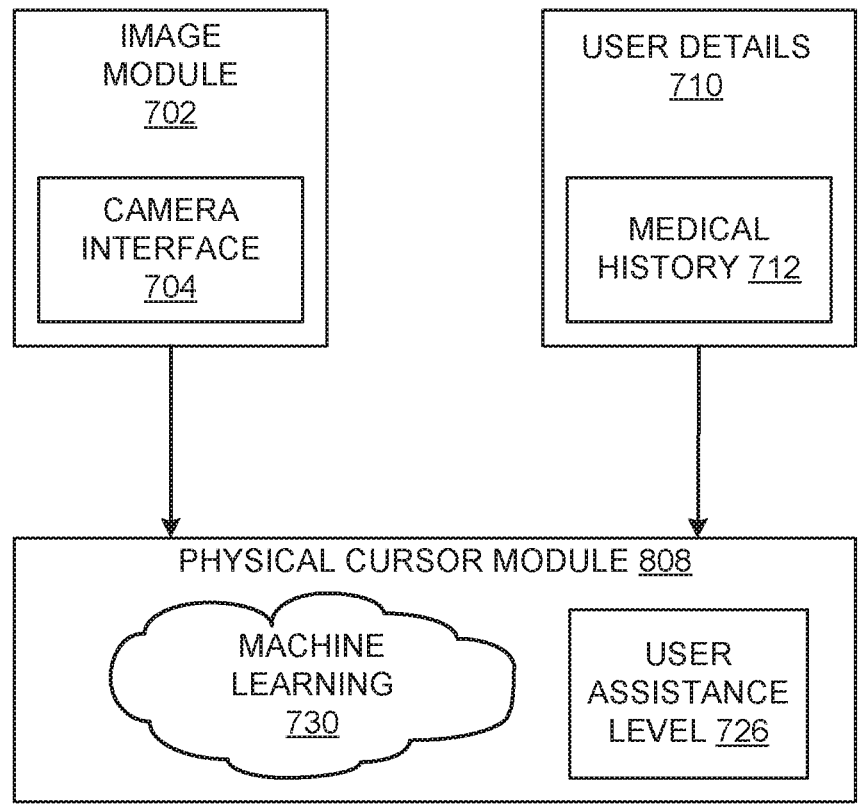
FIG. 7 shows a block diagram of the inputs and machine learning model of a physical cursor module for determining user characteristics and the level of assistance needed.

Referring to FIG. 7, a diagram showing examples of components or modules of a custom process and hardware components according to at least one embodiment. According to one embodiment, the process may include physical cursor module 808 which utilizes supervised machine learning 730 to determine the level of user assistance needed based on a potential medical reason or the analysis of images. The image module 702 may include a camera interface 704 to process images of the user taken with a camera for use in the analysis of driver state. For instance, processing of images taken by a camera may be used to determine that the user is not looking at the display and may need assistance to navigate the physical cursor 206 to an input location. The physical cursor module 808 may also analyze user details 710. For example, the user may have had trouble moving their hand in the past and needed assistance to move the physical cursor 206 to an input location. The physical cursor module 808 may also analyze a user's medical history 712. For instance, the user may have a medical condition that makes it difficult to move their hand or may be taking medications that tend to interfere with their dexterity, as described above in 604. The physical cursor module 808 uses the above information to determine the level of assistance 726 that a user requires to move a physical cursor 208 from a touchpoint 206 to an input location.

Figure 8:
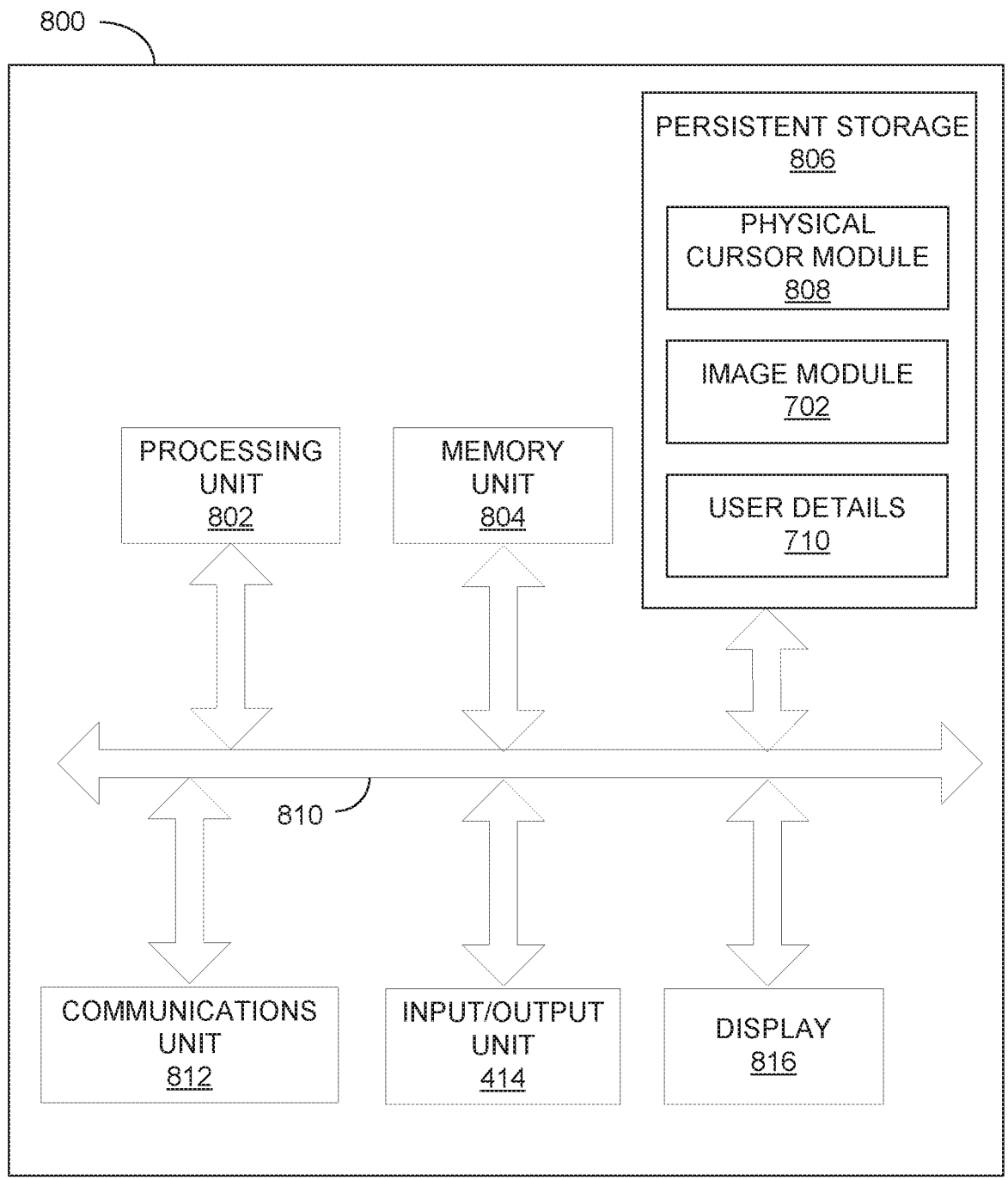
FIG. 8 is a block diagram of an example computer system in which various embodiments may be implemented.

Referring now to FIG. 8, there is shown a block diagram illustrating a computer system 800 according to an embodiment. As shown, a computer system 800 includes a processor unit 802, a memory unit 804, a persistent storage 806, a communications unit 812, an input/output unit 814, a display 816, and a system bus 810. Data, such as user details 710 may be stored in persistent storage 806. In addition, computer programs such as physical cursor module 808 and image module 702 may also be stored in the persistent storage 806 until they are needed for execution, at which time the programs are brought into the memory unit 804 so that they can be directly accessed by the processor unit 802. The processor unit 802 selects a part of memory unit 804 to read and/or write by using an address that the processor 802 gives to memory 804 along with a request to read and/or write. Usually, the reading and interpretation of an encoded instruction at an address causes the processor 802 to fetch a subsequent instruction, either at a subsequent address or some other address. The processor unit 802, memory unit 804, persistent storage 806, communications unit 812, input/output unit 814, and display 816 interface with each other through the system bus 810. The input/output unit 814 may interface with a camera or other devices suitable for capturing ultrasound or infrared images (not shown).

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method for physically assisting in identification of an input location on a touchscreen, the method comprising:
    identifying a plurality of input locations on the touchscreen;
    detecting that a user has contacted the touchscreen at an initial touch point with a pointing device;
    predicting the input location from the plurality of input locations on the touchscreen;
    determining a path from the initial touch point to a predicted input location;
    generating a raised portion of the touchscreen at a location proximate to the initial touch point;
    determining that a current pointing device location is not on the path; and
    moving the raised portion of the touchscreen such that the pointing device is guided to the path.

2. The computer-implemented method of claim 1, wherein the pointing device is a finger of a user.

3. The computer-implemented method of claim 1, further comprising predicting a level of dexterity of the user.

4. The computer-implemented method of claim 1, further comprising:
    detecting a level of dexterity of the user; and
    predicting an assistance requirement for the user based on a detected level of dexterity.

5. The computer-implemented method of claim 4, wherein a machine learning model that predicts user attention based on user patterns while controlling a cursor is used to detect the level of dexterity of the user.

6. The computer-implemented method of claim 1, wherein the generating the raised portion of the touchscreen further comprises generating the raised portion on a front side of the pointing device between a touchpoint and the input location.

7. The computer-implemented method of claim 1, wherein the generating the raised portion of the touchscreen further comprises generating the raised portion on a back side of the pointing device between a touchpoint and the input location.

8. The computer-implemented method of claim 1, wherein the generating the raised portion of the touchscreen further comprises generating the raised portion on two or more sides of the pointing device.

9. A computer system that physically assists in identification of an input location on a touchscreen, the computer system comprising:
    a processor and a memory;
    a touchscreen display that includes microfluidics, wherein in response to an instruction from the processor, fluid is selectively applied to a portion of the touchscreen to raise the portion of the touchscreen;

one or more computer readable storage media having program instructions executable by the processor to perform operations comprising:
  identifying a plurality of input locations on the touchscreen;
  detecting that a user has contacted the touchscreen at an initial touch point with a pointing device;
  predicting the input location from the plurality of input locations on the touchscreen;
  determining a path from the initial touch point to a predicted input location;
  generating a raised portion of the touchscreen at a location proximate to the initial touch point;
  determining that a current pointing device location is not on the path; and
  moving the raised portion of the touchscreen such that the pointing device is guided to the path.

10. The computer system of claim 9, wherein the pointing device is a finger of a user.

11. The computer system of claim 9, further comprising predicting a level of dexterity of the user.

12. The computer system of claim 9, further comprising:
  detecting a level of dexterity of the user; and
  predicting an assistance requirement for the user based on a detected level of dexterity.

13. The computer system of claim 12, wherein a machine learning model that predicts user attention based on user patterns while controlling a cursor is used to detect the level of dexterity of the user.

14. The computer system of claim 9, wherein the generating the raised portion of the touchscreen further comprises generating the raised portion on a front side of the pointing device between a touchpoint and the input location.

15. The computer system of claim 9, wherein the generating the raised portion of the touchscreen further comprises generating the raised portion on a back side of the pointing device between a touchpoint and the input location.

16. The computer system of claim 9, wherein the generating the raised portion of the touchscreen further comprises generating the raised portion on two or more sides of the pointing device.

17. A computer program product for physically assisting in identification of an input location on a touchscreen, the computer program product comprising:
  a non-transitory computer readable storage medium having computer readable program code embodied therewith, the computer readable program code comprising:
    instructions for identifying a plurality of input locations on the touchscreen;
    instructions for detecting that a user has contacted the touchscreen at an initial touch point with a pointing device;
    instructions for predicting the input location from the plurality of input locations on the touchscreen;
    instructions for determining a path from the initial touch point to a predicted input location;
    instructions for generating a raised portion of the touchscreen at a location proximate to the initial touch point;
    instructions for determining that a current pointing device location is not on the path; and
    instructions for moving the raised portion of the touchscreen such that the pointing device is guided to the path.

18. The computer program product of claim 17, further comprising instructions for predicting a level of dexterity of the user.

19. The computer program product of claim 17, further comprising:
  instructions for detecting a level of dexterity of the user; and
  instructions for predicting an assistance requirement for the user based on a detected level of dexterity.

20. The computer program product of claim 19, wherein a machine learning model that predicts user attention based on user patterns while controlling a cursor is used to detect the level of dexterity of the user.

* * * * *